(12) United States Patent
Krüger et al.

(10) Patent No.: US 12,340,892 B2
(45) Date of Patent: Jun. 24, 2025

(54) METHOD AND SYSTEM FOR SUPPORTING HF AND/OR US SURGICAL PROCEDURES AND SOFTWARE PROGRAM PRODUCT

(71) Applicant: OLYMPUS Winter & Ibe GmbH, Hamburg (DE)

(72) Inventors: Jens Krüger, Eichwalde (DE); Fabian Janich, Potsdam (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 106 days.

(21) Appl. No.: 17/192,313

(22) Filed: Mar. 4, 2021

(65) Prior Publication Data

US 2021/0280294 A1 Sep. 9, 2021

(30) Foreign Application Priority Data

Mar. 4, 2020 (DE) ..................... 10 2020 105 834.9

(51) Int. Cl.
*G16H 20/40* (2018.01)
*G16H 10/40* (2018.01)

(52) U.S. Cl.
CPC ............. *G16H 20/40* (2018.01); *G16H 10/40* (2018.01)

(58) Field of Classification Search
CPC ............................... G16H 20/40; G16H 10/40
See application file for complete search history.

(56) References Cited

U.S. PATENT DOCUMENTS

| | | | | |
|---|---|---|---|---|
| 9,247,982 | B2 * | 2/2016 | Fritz | A61B 18/00 |
| 9,788,907 | B1 * | 10/2017 | Alvi | G11B 27/34 |
| 2006/0236242 | A1 * | 10/2006 | Boukhny | A61F 9/00745 715/700 |
| 2007/0239488 | A1 * | 10/2007 | DeRosso | G16H 30/20 705/3 |
| 2009/0049397 | A1 * | 2/2009 | Boukhny | G16H 40/63 715/778 |
| 2014/0081659 | A1 | 3/2014 | Nawana et al. | |
| 2015/0073816 | A1 * | 3/2015 | Ha | G16H 50/70 705/2 |
| 2019/0206563 | A1 * | 7/2019 | Shelton, IV | A61B 17/1285 |

(Continued)

FOREIGN PATENT DOCUMENTS

| | | |
|---|---|---|
| EP | 3 028 657 A1 | 6/2016 |
| WO | 2010/129916 A2 | 11/2010 |

*Primary Examiner* — Steven G. S. Sanghera
(74) *Attorney, Agent, or Firm* — Oliff PLC

(57) ABSTRACT

Disclosed herein are a method and a system for supporting HF and/or US surgical procedures which are carried out using a plurality of HF and/or US surgical instruments. HF and/or US generators are capable of supplying HF and/or US power to the surgical instruments in HF and/or US modes with predetermined operating parameter sets. The generators can be equipped with a measuring device designed to measure electrical properties of treated tissue. The method can include recording and temporarily storing data in the generators, transferring the data to a central analysis device, storing and analyzing the data in the central analysis device, and as a result of the analysis, adapting or rejecting an existing HF and/or US mode, generating a new HF and/or US mode, checking and optionally adapting a laboratory test for relevance to a practical application, and introducing a new laboratory test for a previously unknown surgical state.

20 Claims, 1 Drawing Sheet

(56) References Cited

U.S. PATENT DOCUMENTS

2021/0007760 A1* 1/2021 Reisin .................... G16H 40/63
2021/0065870 A1* 3/2021 Spooner ............... A61B 5/1128
2023/0027978 A1* 1/2023 Gaborit .................. G16H 50/20

* cited by examiner

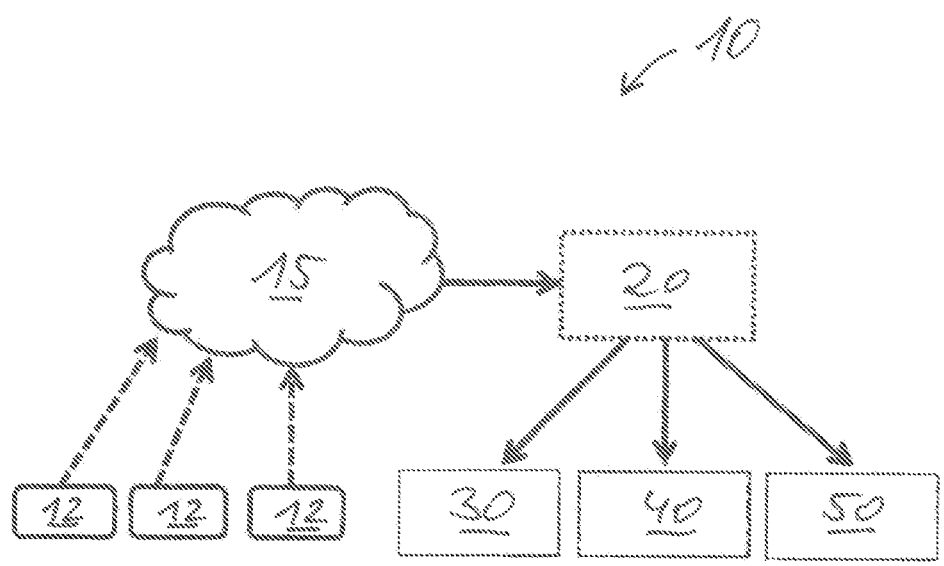

METHOD AND SYSTEM FOR SUPPORTING HF AND/OR US SURGICAL PROCEDURES AND SOFTWARE PROGRAM PRODUCT

TECHNICAL FIELD

The present disclosure relates to a method and a system for supporting high-frequency (HF) and/or ultrasound (US) surgical procedures which are carried out using a plurality of, in particular endoscopic, HF and/or US surgical instruments, which are operated by HF and/or US generators which supply the HF and/or US power in HF and/or US modes with predetermined operating parameter sets, as well as a computer program product.

BACKGROUND

In HF surgery (high-frequency surgery), procedures are performed on patients during which a high-frequency electrical power is introduced into the tissue to be treated, to cut the tissue, or to coagulate it, by means of, in particular endoscopic, HF instruments. For this purpose, the HF instruments have monopolar or bipolar HF electrodes at the distal tip of their endoscope shaft. The HF power is supplied by HF generators such as the Olympus ESG generator family, to which the HF instruments are connected. Complex measurement technology is installed in the HF generators in order to be able to record any state of the tissue and the instrument, for example but not limited to the resistance of the tissue, current and voltage characteristics, the power output, the duration of an application, or the number of activations. These data can be read out in real-time to a development unit via an internal development software and can be used for mode development, i.e., the development of operating parameter sets which can then be supplied and selected on the HF generator for specific applications. Mode development has thus far only taken place during the development phase of an HF generator based on laboratory tests, animal testing substitution models, or based on animal testing.

The development of a new HF mode takes place over many iterations. The more real surgical situations are known and can be replicated in the laboratory, the better the HF mode can be optimized for application by the user. Information about the type and manner of application is introduced into the development via the product management, which is in contact with the users. With this type of communication, no or inadequate measurement values are being transmitted, there is imprecision in the information transferred, or significant information is left out. Accordingly, often detailed information about the behavior of the treated tissue is missing, for example. Such incomplete or imprecise information and data result in an inability to optimize the animal testing substitution models and to create a numerical model for the simulation of tissue. This makes the development of new HF modes or the improvement of existing HF modes very complex. For this reason, it is attempted in the development to reproduce all, including potentially even unnecessary, surgical situations. On the other hand, even such modes are optimized that will possibly not be used in practice.

The result of this development process is that the optimum HF modes, i.e., the optimum operating parameter sets, are not always available for surgical HF procedures on the HF generators.

By analogy, it is also possible to use ultrasound (US) in endoscopic or open surgical applications to treat tissue. In this field, too, ultrasound is generated and controlled as needed for the application. There are also instruments that supply both HF and US power, for example the applicant's Thunderbeat system. The development of new and improved US modes faces the same challenges as the development of HF modes described above.

SUMMARY

It is therefore the object of the present disclosure to improve HF and/or US surgical procedures.

This object is solved by a method for supporting HF and/or US surgical procedures which are carried out using a plurality of HF and/or US surgical instruments, such as endoscopic instruments, which are configured to receive HF and/or US power supplied by HF and/or US generators. The method includes:
  a) recording and temporarily storing data in the HF and/or US generators;
  b) transferring the temporarily stored data to a central analysis device;
  c) storing and analyzing the transferred data in the central analysis device, and
  d) as a result of the analysis, performing at least one of: adapting or rejecting existing HF and/or US mode(s), generating new HF and/or US mode(s), checking laboratory test(s) for relevance to practical application(s) and optionally adapting the laboratory test(s), and introducing new laboratory test(s) for previously unknown surgical state(s).

In the context of the present disclosure, endoscopic devices are understood as not only endoscopes in the narrower sense but generally such instruments as are used in an endoscope-like manner, for example but not limited to laparoscopes.

The HF and/or US generators are equipped with an electrical measuring device that is designed to carry out measurements of electrical properties of treated tissue during the surgical procedures, and the HF and/or US generators are designed to supply HF and/or US power to one or more of the plurality of HF and/or US surgical instruments in HF and/or US modes with predetermined operating parameter sets. The data can include surgical data and/or measurement data collected by the electrical measuring device.

The disclosure is based on the fundamental concept that, for the first time, data from real surgeries are supplied in order to draw conclusions regarding the use and the suitability of HF and/or US modes of HF and/or US generators and to change and adapt them as needed.

To make this possible, several interlocking changes in the existing systems are necessary. Regarding hardware, the HF and/or US generators are equipped to temporarily store data such as surgical data and measurement data and to transmit them to a central analysis device. This modification of the HF and/or US generators, which thus far can only be read out by means of a directly connected development unit, ensures that data from real HF and/or US surgical procedures are collected and supplied for the analysis. The second change relates to the set-up of a central analysis device which collects and analyzes the transmitted data from a plurality of HF and/or US generators.

An application example of this is an HF generator system of a manufacturer whose HF generators are equipped with the corresponding functionalities, for example with a temporary storage unit and a transmission unit. The HF generators sold and installed by the manufacturer are set up in such a way as to return their data, anonymized if applicable, to a central computer or a central data processing system at the manufacturer's, which operates as an analysis device so that the manufacturer has access to the data transmitted by the HF generators regarding the surgeries and can use these data for analysis and for improving and changing HF modes and, if applicable, for adapting the laboratory tests. This applies by analogy to a US generator system or a hybrid HF and US system.

In embodiments, anonymized patient data, in particular success and/or recovery data, type of the procedure, duration of the procedure, an evaluation or assessment of the procedure by a user and/or metadata of the HF and/or US modes used, are recorded and temporarily stored as surgical data in a method step a). The evaluation or assessment of the procedure by a user, for example a surgeon, can take place in the form of an assessment as "good" or "bad", or based on an evaluation of the treatment success, for example whether a blood vessel was successfully sealed, which is in some cases difficult to evaluate based on the measurement data only. The metadata of the HF and/or US modes used relate for example to the set operating parameters, which can correspond with the preset operating parameter sets of the HF and/or US modes, but in individual cases can also be modified by the attending medical practitioner or a person tasked before or during the surgery with the operation of the HF and/or US generator. The metadata can also comprise data such as location, times, and instrument-specific data. These data are thus either basic data of the surgery or settings of the instruments involved, but not data that are measured by a measuring device during the surgery. The data to be recorded in this context as surgical data are not limited to the cases stated here and can be supplemented with suitable other data.

For variable data to be measured, in embodiments, an impedance or a resistance of the treated tissue, current and voltage characteristics, power output, duration of the application, number of activations, temperatures of the treated tissue, or types of treated tissue, in particular in a time correlation with the used HF and/or US mode and/or HF and/or US power introduced are recorded and temporarily stored as measurement data in method step a). The data to be recorded in this context as measurement data are not limited to the cases stated here and can be supplemented with suitable other data.

The combination of the recording of the surgical data and the measurement data is particularly advantageous for the assessment of the suitability of the HF and/or US modes used in real surgeries.

In embodiments, the transfer in method step b) takes place via a digital, in particular wireless, interface and infrastructure. As a digital infrastructure, the internet and also local area networks (LANs) are possible. An at least partly wireless transfer can for example be carried out via WLAN (WiFi) or mobile 4G or 5G data connections or similar.

In method step c), a data consolidation, an extraction of data and/or features, an analysis by means of machine learning, and/or an analysis by means of data mining take place in embodiments. A data consolidation in the context of the present disclosure is understood as converting the data of the different HF generators, in particular if there are different models, into a common data format, which then establishes mutual comparability of the data. For example, an analysis is performed during the extraction of data and features with a part of the data which fulfill different filtering requirements of only a part of the data or features that are particularly relevant to the purpose of the analysis, which clearly limits the computing requirements. Machine learning and data mining can for example find out on the basis of treatment results which operating parameter settings lead to particularly good results in which situations.

An application example of data and features that can be extracted in the context of the analysis and their application is the measured tissue impedance. This impedance can be used for an automated tissue recognition since different tissue types have different electrical properties. The regulating of the HF voltage can also have to be adapted as a result of the measured tissue impedance, wherein a higher voltage must in some cases be set for a high-ohmic working range, if appropriate. A phase shift between current and voltage of the HF signal can be used to examine the influence of endoscopes on the measurement system used and afterwards the measuring accuracy can be improved. By extracting and analyzing the characteristic of the tissue impedance, the control speed can be optimized. With fast load variations, the regulator must in some cases be set to respond faster. This list of potential application cases is not complete.

With machine learning, the purpose is to extract specific dependencies and features from the largest possible quantity of training data. This creates a statistical model of these data. Alternatively, data mining approaches can also be used in order to be able to identify new interconnections. Data can also be stored in their raw form in order to gain features therefrom. Such data can for example be log information of the generator, live recordings of the use from the graphical user interface (GUI), measurement data of the generator such as output, voltage, or resistance, instrument data or activation channel information such as for example whether or how long a foot switch is being pressed.

Application examples of this comprise resistance and output characteristics for specific surgeries from which a statistical model for these HF modes or the treated tissue can be developed, or voltage characteristics of the internal components from which it can be determined whether the power reserves of the generator can be optimized for specific HF modes or instruments. Based on a power output profile, the usability of HF modes can be deduced, for example how a medical practitioner uses an HF mode, whether the practitioner can handle the power output, whether the practitioner stops frequently or has to restart the procedure. Based on the information whether specific error messages are triggered or whether undesirable states occur inside the generator during a surgery, improvements of the usability of the HF modes can be developed that will for example reduce error frequency or adapt error thresholds. Other questions are whether there are interruptions in the work sequence, or if the medical practitioner does not find a specific setting and searches through the menus. These analyses and questions can, depending on the application, be performed for example with neural networks or conventional statistical methods since the questions are well defined.

In embodiments, an HF mode is adapted in method step d) if, due to the transferred data of several HF generators, it is found that operating parameters of an HF mode used must be adapted for the intended use to improve the use. This can be identified for example, where some medical practitioners or other operating personnel at first select a specific HF mode for specific types of surgeries, but after the selection of the HF modes systematically change individual operating parameters, a comparison with other surgeries during which these changes did not take place show that the treatment results are better because of the systematic changes. On the other hand, it is possible that the requested output or the requested output profile with specific surgeries does not correspond with the one that is actually provided for a specific HF mode. For example, if a badly adapted HF mode is used, a coagulation seam can be generated that is not suitable for the treated tissue. Here, an adaptation is made in the direction that the outputs or output profiles measured during the real surgeries are better implemented in the HF mode. These statements apply by analogy to US modes.

In other embodiments, an existing HF and/or US mode is rejected in method step d) if it is found based on the transferred data of several HF and/or US generators that the HF and/or US mode is not used or is used with less than a predetermined frequency or a predetermined usage share. Furthermore, in embodiments, new HF and/or US modes can be generated in method step d) if, due to the transferred data of several HF and/or US generators, it is found that the operating parameter sets of the existing HF and/or US modes are not suitable for newly identified fields of use. Corresponding to the changes in HF and/or US modes, the last-stated case can for example be identified by the fact that an output or an output profile is used that does not correspond with the actually desired profile of the selected HF and/or US mode, i.e., that it deviates therefrom by a potentially predetermined amount.

These options that can be used alternatively to or cumulatively with one another result in a further development of the predetermined HF and/or US modes of the HF and/or US generators. The changes in HF and/or US modes are transmitted in embodiments to the existing HF and/or US generators and implemented in the HF generators and/or changes in HF and/or US modes are implemented when new HF and/or US generators are manufactured.

In other embodiments, laboratory tests are checked for their relevance to practical applications in method step d) and are then adapted if, due to the transferred data of several HF and/or US generators, it is found that the existing laboratory tests do not replicate the surgical conditions occurring during the real procedures fully or replicate them in a modified form. The laboratory tests are typically performed on test animals or animal testing substitution models, i.e., on organs or body parts removed from animals. Such organs or body parts are dead, non-perfused tissue, for example cattle hearts. During the laboratory tests, the mode parameters for cutting or coagulating are adapted in realtime such that the mode functions optimally on this suitable tissue. This is assessed, among other things, based on a good starting incision behavior, a defined coagulation seam, and a correct regulating behavior. For application inside the body, the tissue impedance is often different in non-perfused tissues, or there are additional parasitic capacitances that the non-perfused tissue cannot replicate. For this reason, the tissue is often connected additionally to suitable load resistors, capacitors, and inductors in order to obtain as good a substitution model as possible. Often, these measures are not sufficient for creating substitution models that closely resemble reality. For this reason, the tests are supplemented with a perfusion circulation if applicable, for example using a pump that pumps pig blood through a pig kidney. Here, too, the mode parameters are evaluated and optimized if necessary.

Overall, however, the problem often persists that the real application scenarios are not known, i.e., among others the magnitude of the tissue impedance, the speed of change of the tissue impedance, or the power settings the equipment is operated with.

In principle, it is being assumed that the corresponding procedures on the test animals or animal testing substitution models in the laboratory will simulate the real procedures on humans in a satisfactory manner. For the reasons stated above, this is not always the case, though. If the measurement data of the HF generators allow for the conclusion that the actual processes and power draws during surgeries on humans deviate from the laboratory conditions, the tests can be changed such that they better approximate the measured conditions. This can also result in a smaller number of test animals being needed for the development of HF and/or US modes.

Furthermore, in embodiments, new laboratory tests for thus far unknown surgical states are introduced in method step d) if, due to the transferred data of several HF and/or US generators, it is found that the HF and/or US generators record surgical states that do not occur in the laboratory tests. This complements the data basis which is available for the development of HF and/or US modes and thereby improves the results obtained with the HF and/or US generators with the corresponding equipment.

The object of the disclosure is also solved by a system for supporting HF and/or US surgical procedures, comprising a plurality of HF and/or US surgical instruments, such as endoscopic instruments, a plurality of HF and/or US generators, and at least one central analysis device. The HF and/or US generators are designed to each operate one or more of the HF and/or US surgical instruments and to supply HF and/or US power in HF and/or US modes with predetermined operating parameter sets. The HF and/or US generators are each equipped with an electrical measuring device in order to perform measurements of electrical properties of treated tissue during the procedures, and the HF and/or US generators are designed and configured to temporarily store data and transmit them to the at least one central analysis device. The central analysis device is designed and configured to store and analyze the transferred data and, as a result of the analysis, adapt or reject existing HF and/or US mode(s), generate new HF and/or US mode (s), check laboratory test(s) for their relevance to practical application(s) and adapt them if necessary, and/or to introduce new laboratory test(s) for thus far unknown surgical state(s). Preferably, the central analysis device is designed and configured to perform the method steps c) and d) of a method according to the disclosure described above.

The system relates to the method according to the disclosure and thus also realizes its features, properties, and advantages.

The object of the disclosure is also solved by a computer program product with program code means that are designed to perform the method steps c) and d) of a method according to the disclosure described above when it is run on an analysis device of a system according to the disclosure described above. For instance, disclosed herein is a non-transitory computer readable storage medium having stored therein a program to be executable by a processor. The program causes the processor to execute storing and analyzing data transmitted from a plurality of HF and/or US generators in a central analysis device, and as a result of the analysis, performing at least one of adapting or rejecting an existing HF and/or US mode, generating a new HF and/or US mode, checking a laboratory test for relevance to practical application and optionally adapting the laboratory test, and introducing a new laboratory test for a previously unknown surgical state. The computer-readable storage medium may include a memory device, Random Access Memory (RAM), or any other suitable device.

The computer program product thus also realizes the features, properties, and advantages of the method according to the disclosure.

Further features of the disclosure will become evident from the description of the inventive embodiments together with the claims and the attached drawing. Embodiments according to the disclosure can fulfill individual features or a combination of several features.

In the scope of the disclosure, features which are designated by "in particular" or "preferably" are understood to be optional features.

BRIEF DESCRIPTION OF THE DRAWING

The exemplary embodiments are described below in reference to the drawing, without restricting the general idea of the disclosure, whereby we expressly refer to the drawing with regard to the disclosure of all details that are not explained in greater detail in the text. The FIGURE shows:

FIG. 1 a schematic representation of a system according to the invention.

DETAILED DESCRIPTION

The following description is based on an HF system but it is transferrable by analogy without limitations to an ultrasound system or a hybrid HF/US system.

FIG. 1 schematically shows a possible configuration of a system 10 according to the invention, which comprises a plurality of HF generators 12 that are equipped according to the invention to temporarily store surgical data and/or measurement data and to transmit them to a central analysis device 15, which has a database for surgical applications. The transmission can occur via the internet and locally, either with a wired connection or via WLAN (WiFi), or even via the mobile 4G network or the 5G network or other suitable communication networks and communication means.

The various HF generators 12 that can be localized in different locations, for example in different cities or countries, in hospitals and medical offices independent from hospitals, are used in a plurality of HF and/or US surgical procedures under a plurality of different conditions and with a plurality of different operating parameter combinations or respectively HF modes. With their measurement electronic system, the HF generators 12 record various measuring variables during the surgery, for example, the power introduced, the resistance of the treated tissue, etc. Also, the HF generators 12 can be connected to the surgery management system of a hospital and receive data on the patient and the planned/performed procedure and also transmit data to the analysis device 15, in anonymized form if applicable.

Due to the plurality of connected HF generators 12 and the plurality of procedures performed with them, the analysis device 15 has a large and steadily growing data basis available based on which it can be checked if the existing HF modes correspond with the requirements of the practical applications, are selected at all, and it can be determined whether the laboratory tests that are used for developing HF modes image reality in adequate form at all. The analysis 20 takes place in the analysis device 15 by means of algorithms that can be structured differently, for example in the form of the recognition of clusters of operating parameters in practical applications and their comparison to existing pre-settings, a comparison of the measurement data to assumed optimum measurement data, also based on a statistical analysis, connected with machine learning if applicable, in which for example a neural network is trained based on training data to recognize favorable and unfavorable treatment progressions.

The analysis 20 can lead to different results. A typical result is an HF mode development 30, i.e., the recognition that improvements are necessary on the existing HF modes, that specific HF modes are superfluous, or that new HF modes must be created. By supplying improved HF modes, the HF and/or US surgical procedures are improved and supported starting at the moment of introduction of the new improved HF modes.

Another consequence of the analysis 20 can be a test bench 40 for HF modes. The data collected during real use can for example serve in a virtual test bench to simulate the recorded surgeries with operating parameters that were changed compared to the real procedures that form the basis, and to make predictions as to the outcome of the procedures as a result of the changes in the operating parameters of the HF generators 12. Such a methodology will save a large number of otherwise necessary animal tests.

Furthermore, laboratory tests themselves can also be adapted to better simulate the progression of actual HF and/or US surgical procedures than had been possible thus far. Laboratory tests that, after comparison with the real data, describe progressions or surgical conditions that do not or hardly ever occur in practical applications can be eliminated, which can also reduce the use of test animals.

Finally, market data 50 can also be extracted from the analysis 20, for example to obtain a better placement or availability of frequently used HF modes in the operating menus of the HF generators 12 and thus render the system better operable for users. This also includes the insight whether HF modes can be eliminated that are not or hardly ever used.

All named features, including those taken from the drawing alone, and individual features, which are disclosed in combination with other features, are considered alone and in combination as essential for the invention. Embodiments according to the invention can be fulfilled by individual features or a combination of several features.

LIST OF REFERENCE NUMBERS

10 System
12 HF generator
15 Analysis device with database for surgical applications
20 Analysis
30 HF mode development
40 Test bench for HF modes
50 Market data

The invention claimed is:

1. A method for supporting high-frequency (HF) and/or ultrasound (US) surgical procedures which are carried out using a plurality of HF and/or US surgical instruments that are configured to receive HF and/or US power supplied by HF and/or US generators, where each of the HF and/or US generators are located at different locations and are responsible for powering separate surgical systems, wherein each surgical system comprises one or more of the plurality of HF and/or US surgical instruments and one of the HF and/or US generators, the method comprising:

a) recording and temporarily storing in the HF and/or US generators data collected from a plurality of the HF and/or US surgical procedures carried out using the plurality of HF and/or US surgical instruments, each of the HF and/or US generators being:

equipped with an electrical measuring device that is configured to carry out measurements of electrical properties of treated tissue during the surgical procedures, and configured to supply HF and/or US power to one or more of the plurality of HF and/or US surgical instruments in HF and/or US modes with predetermined operating parameter sets, the HF and/or US modes being selectable from operating menus of the HF and/or US generators for specific applications during one or more of the HF and/or US surgical procedures, b) transferring the temporarily stored data collected from the plurality of the HF and/or US surgical procedures from the HF and/or US generators to a central analysis device, c) storing and analyzing the transferred data collected from the plurality of the HF and/or US surgical procedures in the central analysis device, wherein a data consolidation, an extraction of data and/or features, an analysis by machine learning, and/or an analysis by data mining take place in method step c), d) as a result of the analysis of the transferred data collected from the plurality of the HF and/or US surgical procedures, performing at least one of:

adapting an existing one of the HF and/or US modes in the operating menus of the HF and/or US generators for a specific application during one or more of the HF and/or US surgical procedures in which the HF and/or US generators supply HF and/or US power to one or more of the plurality of HF and/or US surgical instruments, the adapted one of the HF and/or US modes being saved in the operating menus, and generating a new HF and/or US mode in addition to the HF and/or US modes already available in the operating menus of the HF and/or US generators for a specific application during one or more of the HF and/or US surgical procedures in which the HF and/or US generators supply HF and/or US power to one or more of the plurality of HF and/or US surgical instruments, the new HF and/or US mode being saved in the operating menus, and e) operating one or more of the HF and/or US generators to supply HF and/or US power to one or more of the plurality of HF and/or US surgical instruments in the adapted one of the HF and/or US modes or in the new HF and/or US mode, wherein:

the data collected from the plurality of the HF and/or US surgical procedures includes surgical data and/or measurement data collected by the electrical measuring device, an impedance or a resistance of the treated tissue, current and voltage characteristics, power output, duration of the application, number of activations, temperatures of the treated tissue, or types of the treated tissue are recorded and temporarily stored as the measurement data in method step a), the measurement data is recorded and temporarily stored in a time correlation with the HF and/or US mode and/or the HF and/or US power introduced, and at least one of the following is satisfied:

the analyzing of the transferred data collected from the plurality of the HF and/or US surgical procedures in the central analysis device in step c) is performed by algorithms that recognize clusters of operating parameters in practical applications and compare the clusters of operating parameters to existing pre-settings, the analyzing of the transferred data collected from the plurality of the HF and/or US surgical procedures in the central analysis device in step c) is performed by algorithms that compare the measurement data to assumed optimum measurement data, and the analyzing of the transferred data collected from the plurality of the HF and/or US surgical procedures in the central analysis device in step c) includes a statistical analysis, using machine learning, in which a neural network is trained based on training data to recognize favorable and unfavorable treatment progressions.

2. The method according to claim 1, wherein the plurality of HF and/or US surgical instruments are endoscopic devices.

3. The method according to claim 1, wherein anonymized patient data are recorded and temporarily stored as the surgical data in method step a).

4. The method according to claim 3, wherein the anonymized patient data includes success and/or recovery data, type of procedure, procedure duration, an evaluation or assessment of the procedure by a user, and/or metadata of the HF and/or US modes used.

5. A method for supporting high-frequency (HF) and/or ultrasound (US) surgical procedures which are carried out using a plurality of HF and/or US surgical instruments that are configured to receive HF and/or US power supplied by HF and/or US generators, where each of the HF and/or US generators are located at different locations and are responsible for powering separate surgical systems, wherein each surgical system comprises of one or more of the plurality of HF and/or US surgical instruments and one of the HF and/or US generators, the method comprising:

a) recording and temporarily storing in the HF and/or US generators data collected from a plurality of the HF and/or US surgical procedures carried out using the plurality of HF and/or US surgical instruments, each of the HF and/or US generators being:

equipped with an electrical measuring device that is configured to carry out measurements of electrical properties of treated tissue during the surgical procedures, and configured to supply HF and/or US power to one or more of the plurality of HF and/or US surgical instruments in HF and/or US modes with predetermined operating parameter sets, the HF and/or US modes being selectable from operating menus of the HF and/or US generators for specific applications during one or more of the HF and/or US surgical procedures, b) transferring the temporarily stored data collected from the plurality of the HF and/or US surgical procedures from the HF and/or US generators to a central analysis device, c) storing and analyzing the transferred data collected from the plurality of the HF and/or US surgical procedures in the central analysis device, wherein a data consolidation, an extraction of data and/or features, an analysis by machine learning, and/or an analysis by data mining take place in method step c), d) as a result of the analysis of the transferred data collected from the plurality of the HF and/or US surgical procedures, performing at least one of:

adapting an existing one of the HF and/or US modes in the operating menus of the HF and/or US generators for a specific application during one or more of the HF and/or US surgical procedures in which the HF and/or US generators supply HF and/or US power to one or more of the plurality of HF and/or US surgical instruments, the adapted one of the HF and/or US modes being saved in the operating menus, and generating a new HF and/or US mode in addition to the HF and/or US modes already available in the operating menus of the HF and/or US generators for a specific application during one or more of the HF and/or US surgical procedures in which the HF and/or US generators supply HF and/or US power to one or more of the plurality of HF and/or US surgical instruments, the new HF and/or US mode being saved in the operating menus, and e) operating one or more of the HF and/or US generators to supply HF and/or US power to one or more of the plurality of HF and/or US surgical instruments in the adapted one of the HF and/or US modes or in the new HF and/or US mode, wherein the transfer in method step b) takes place via a digital interface and infrastructure, and wherein at least one of the following is satisfied:

the analyzing of the transferred data collected from the plurality of the HF and/or US surgical procedures in the central analysis device in step c) is performed by algorithms that recognize clusters of operating parameters in practical applications and compare the clusters of operating parameters to existing presettings, the analyzing of the transferred data collected from the plurality of the HF and/or US surgical procedures in the central analysis device in step c) is performed by algorithms that compare the measurement data to assumed optimum measurement data, and the analyzing of the transferred data collected from the plurality of the HF and/or US surgical procedures in the central analysis device in step c) includes a statistical analysis, using machine learning, in which a neural network is trained based on training data to recognize favorable and unfavorable treatment progressions.

6. The method according to claim 5, wherein the digital interface and infrastructure is wireless.

7. The method according to claim 1, wherein the existing one of the HF and/or US modes is adapted in method step d) if, due to the transferred data of several of the HF and/or US generators, it is found that operating parameters of the existing one of the HF and/or US modes should be adapted for an intended use during one or more of the HF and/or US surgical procedures to improve the intended use.

8. The method according to claim 1, wherein the new HF and/or US mode is generated in method step d) if, due to the transferred data of several of the HF and/or US generators, it is found that the operating parameter sets of existing HF and/or US modes are not suitable for newly identified fields of use.

9. The method according to claim 1, further comprising:
transmitting changes in the HF and/or US modes to the HF and/or US generators and implementing the changes in the HF and/or US generators, and/or
implementing changes in the HF and/or US modes when a new HF and/or US generator is manufactured.

10. The method according to claim 1, wherein as a result of the analysis of the transferred data collected from the plurality of the HF and/or US surgical procedures, method step d) further comprises:
adapting a laboratory test for improved relevance to a practical application during one or more of the HF and/or US surgical procedures in which the HF and/or US generators supply HF and/or US power to one or more of the plurality of HF and/or US surgical instruments if, due to the transferred data of several of the HF and/or US generators, it is found that the laboratory test does not replicate surgical conditions occurring during real procedures fully or replicate the surgical conditions in a modified form.

11. The method according to claim 1, wherein as a result of the analysis of the transferred data collected from the plurality of the HF and/or US surgical procedures, method step d) further comprises:
introducing a new laboratory test for a previously unknown surgical state that can occur during at least one of the HF and/or US surgical procedures in which the HF and/or US generators supply HF and/or US power to one or more of the plurality of HF and/or US surgical instruments if, due to the transferred data of several of the HF and/or US generators, it is found that the HF and/or US generators record a surgical state that does not occur in laboratory tests.

12. A system for supporting high-frequency (HF) and/or ultrasound (US) surgical procedures, comprising:
a plurality of HF and/or US surgical instruments,
a plurality of HF and/or US generators that are:
each located at different locations and are responsible for powering separate surgical systems, wherein each surgical system comprises one or more of the plurality of HF and/or US surgical instruments and one of the HF and/or US generators,
each equipped with an electrical measuring device configured to perform measurements of electrical properties of treated tissue during the procedures, and
each configured to supply HF and/or US power to one or more of the HF and/or US surgical instruments in HF and/or US modes with predetermined operating parameter sets, the HF and/or US modes being selectable from operating menus of the HF and/or US generators for specific applications during one or more of the HF and/or US surgical procedures, and
a central analysis device, wherein:
the HF and/or US generators are configured to:
temporarily store data collected from a plurality of the HF and/or US surgical procedures carried out using the plurality of HF and/or US surgical instruments, and
transmit the data to the central analysis device,
the central analysis device is configured to:
store and analyze the transmitted data collected from the plurality of the HF and/or US surgical procedures, the storing and analyzing including a data consolidation, an extraction of data and/or features, an analysis by machine learning and/or an analysis by data mining, and
as a result of the analysis of the transmitted data collected from the plurality of the HF and/or US surgical procedures, perform at least one of:
adapt an existing one of the HF and/or US modes in the operating menus of the HF and/or US generators for a specific application during one or more of the HF and/or US surgical procedures in which the HF and/or US generators supply HF and/or US power to one or more of the plurality of HF and/or US surgical instruments, and save the adapted one of the HF and/or US modes in the operating menus, and generate a new HF and/or US mode in addition to the HF and/or US modes already available in the operating menus of the HF and/or US generators for a specific application during one or more of the HF and/or US surgical procedures in which the HF and/or US generators supply HF and/or US power to one or more of the plurality of HF and/or US surgical instruments, and save the new HF and/or US mode in the operating menus, the HF and/or US generators supply HF and/or US power to one or more of the HF and/or US surgical instruments in the adapted one of the HF and/or US modes or in the new HF and/or US mode, and at least one of the following is satisfied:
  the central analysis device is configured to analyze the transmitted data collected from the plurality of the HF and/or US surgical procedures by means of algorithms that recognize clusters of operating parameters in practical applications and compare the clusters of operating parameters to existing pre-settings, and
  the data collected from the plurality of the HF and/or US surgical procedures includes measurement data collected by the electrical measuring device, and the central analysis device is configured to analyze the transmitted data collected from the plurality of the HF and/or US surgical procedures by means of algorithms that compare the measurement data to assumed optimum measurement data, and
  the central analysis device is configured to analyze the transmitted data collected from the plurality of the HF and/or US surgical procedures by performing a statistical analysis, using machine learning, in which a neural network is trained based on training data to recognize favorable and unfavorable treatment progressions.

13. A non-transitory computer readable storage medium having stored therein a program to be executable by a processor, the program causing the processor to execute:
  storing and analyzing data transmitted from a plurality of high-frequency (HF) and/or ultrasound (US) generators in a central analysis device, the data being collected from a plurality of HF and/or US surgical procedures performed using a plurality of HF and/or US surgical instruments that receive HF and/or US power supplied by the HF and/or US generators in HF and/or US modes with predetermined operating parameter sets, wherein each of the HF and/or US generators are located at different locations and are responsible for powering separate surgical systems, wherein each surgical system comprises one or more of the plurality of HF and/or US surgical instruments and one of the HF and/or US generators, the HF and/or US modes being selectable from operating menus of the HF and/or US generators for specific applications during one or more of the HF and/or US surgical procedures, the storing and analyzing including a data consolidation, an extraction of data and/or features, an analysis by machine learning and/or an analysis by data mining,
  as a result of the analysis of the data transmitted from the plurality of HF and/or US generators, performing at least one of:
    adapting an existing one of the HF and/or US modes in the operating menus of the HF and/or US generators for a specific application during one or more of the HF and/or US surgical procedures in which the HF and/or US generators supply HF and/or US power to one or more of the plurality of HF and/or US surgical instruments, and saving the adapted one of the HF and/or US modes in the operating menus, and
    generating a new HF and/or US mode in addition to the HF and/or US modes already available in the operating menus of the HF and/or US generators for a specific application during one or more of the HF and/or US surgical procedures in which the HF and/or US generators supply HF and/or US power to one or more of the plurality of HF and/or US surgical instruments, and saving the new HF and/or US mode in the operating menus, and
  causing one or more of the HF and/or US generators to supply HF and/or US power to one or more of the HF and/or US surgical instruments in the adapted one of the HF and/or US modes or in the new HF and/or US mode,
  wherein at least one of the following is satisfied:
    the analyzing of the transmitted data collected from the plurality of the HF and/or US surgical procedures is performed by means of algorithms that recognize clusters of operating parameters in practical applications and compare the clusters of operating parameters to existing pre-settings, and
    the data collected from the plurality of the HF and/or US surgical procedures includes measurement data collected by the electrical measuring device, and the analyzing of the transmitted data collected from the plurality of the HF and/or US surgical procedures is performed by means of algorithms that compare the measurement data to assumed optimum measurement data, and
    the analyzing of the transmitted data collected from the plurality of the HF and/or US surgical procedures includes performing a statistical analysis, using machine learning, in which a neural network is trained based on training data to recognize favorable and unfavorable treatment progressions.

14. The method according to claim 1, wherein the analyzing of the transferred data collected from the plurality of the HF and/or US surgical procedures in the central analysis device in step c) is performed by algorithms that recognize clusters of operating parameters in practical applications and compare the clusters of operating parameters to existing pre-settings.

15. The method according to claim 1, wherein the analyzing of the transferred data collected from the plurality of the HF and/or US surgical procedures in the central analysis device in step c) is performed by algorithms that compare the measurement data to assumed optimum measurement data.

16. The method according to claim 1, wherein the analyzing of the transferred data collected from the plurality of the HF and/or US surgical procedures in the central analysis device in step c) includes a statistical analysis, using machine learning, in which a neural network is trained based on training data to recognize favorable and unfavorable treatment progressions.

17. The method according to claim 5, wherein the analyzing of the transferred data collected from the plurality of the HF and/or US surgical procedures in the central analysis device in step c) is performed by algorithms that recognize clusters of operating parameters in practical applications and compare the clusters of operating parameters to existing pre-settings.

18. The system according to claim 12, wherein the central analysis device is configured to analyze the transmitted data collected from the plurality of the HF and/or US surgical procedures by means of algorithms that recognize clusters of operating parameters in practical applications and compare the clusters of operating parameters to existing pre-settings.

19. The system according to claim 12, wherein the data collected from the plurality of the HF and/or US surgical procedures includes measurement data collected by the electrical measuring device, and the central analysis device is configured to analyze the transmitted data collected from the plurality of the HF and/or US surgical procedures by means of algorithms that compare the measurement data to assumed optimum measurement data.

20. The system according to claim 12, wherein the central analysis device is configured to analyze the transmitted data collected from the plurality of the HF and/or US surgical procedures by performing a statistical analysis, using machine learning, in which a neural network is trained based on training data to recognize favorable and unfavorable treatment progressions.

* * * * *